United States Patent [19]
Niskin

[11] 3,969,925
[45] July 20, 1976

[54] IN SITU OCEANOGRAPHIC SAMPLE SEPARATOR

[75] Inventor: Shale Jack Niskin, Miami, Fla.

[73] Assignee: The United States of America as represented by the Secretary of the Navy, Washington, D.C.

[22] Filed: Sept. 16, 1975

[21] Appl. No.: 613,843

[52] U.S. Cl. .............................. 73/61 R; 73/170 A; 73/425.4 R
[51] Int. Cl.² ....................................... G01N 15/00
[58] Field of Search ........ 73/61, 61.4, 170, 425.4 R, 73/425.6

[56] References Cited
UNITED STATES PATENTS

| | | |
|---|---|---|
| 3,085,425 | 4/1963 | Roman .............................. 73/425.6 |
| 3,531,995 | 10/1970 | Barker .............................. 73/425.4 |
| 3,892,130 | 7/1975 | Winget .............................. 73/425.4 |

*Primary Examiner*—S. Clement Swisher
*Attorney, Agent, or Firm*—R. S. Sciascia; L. I. Shrago; C. E. Vautrain, Jr.

[57] ABSTRACT

A sampler for in situ oceanographic investigation is provided. At any desired depth, water is drawn into the sampler, treated with a desired liquid, and expelled from the sampler by gas pressure. Any particulate matter in the sample is retained on a filter of desired pore size.

17 Claims, 3 Drawing Figures

IN SITU OCEANOGRAPHIC SAMPLE SEPARATOR

The present invention relates to oceanographic sampling and, more particularly, to a water sampler in which particulate matter is separated in situ from a water sample.

There are many different water collectors in use for obtaining deep ocean and other samples. There are, however, situations where no existing collector will properly serve a desired function. For example, water samples in most investigations must be brought to the surface where particulate matter therein is separated, treated, and then lowered again for a period of incubation at the natural depth environment. This procedure subjects the particulate matter sample to changing environmental conditions as well as to possible contamination. Since separation of the samples from the captured water is usually conducted in a laboratory, an additional opportunity for contamination is introduced. The particulate separator of the present invention avoids the foregoing and other disadvantages of conventional samplers by removing the sample in situ at any time during the operation without requiring removal from the sampling depth. The separator of the invention also injects a tracer liquid into the water sample and separates the free water phase from the labeled particulate matter after any desired time of incubation.

Accordingly, it is an object of the present invention to provide for the removal of particulate matter at any desired sampling depth.

Another object of this invention is to provide an in situ oceanographic sample separator wherein particulate matter may be labeled and removed at the sampling depth.

A further object of this invention is to provide an in situ sample separator which permits incubation of separated particulate matter for any desired period of time at the sampling depth.

Other objects, advantages and novel features of the invention will become apparent from the following detailed description thereof when considered in conjunction with the accompanying drawings in which like numerals represent like parts throughout and wherein.

The present invention, in general, concerns a sampling device for in situ oceanographic investigations which includes a sample chamber in which water samples are received and exited by a dual-valve arrangement. The valves are messenger-actuated in two discrete steps, the first step involving actuating the sampler, filling its chamber with water, injecting a tracer solution, and allowing the particulate sample matter to incubate. The second step, independently messenger-actuated, causes the release of compressed gas into the chamber via a manifold, forcing the contained water out through an appropriate filter after which the sampling device is recovered empty of all contents except whatever particulate matter has been collected by the filter which matter is immediately ready for laboratory analysis.

Figure 1:
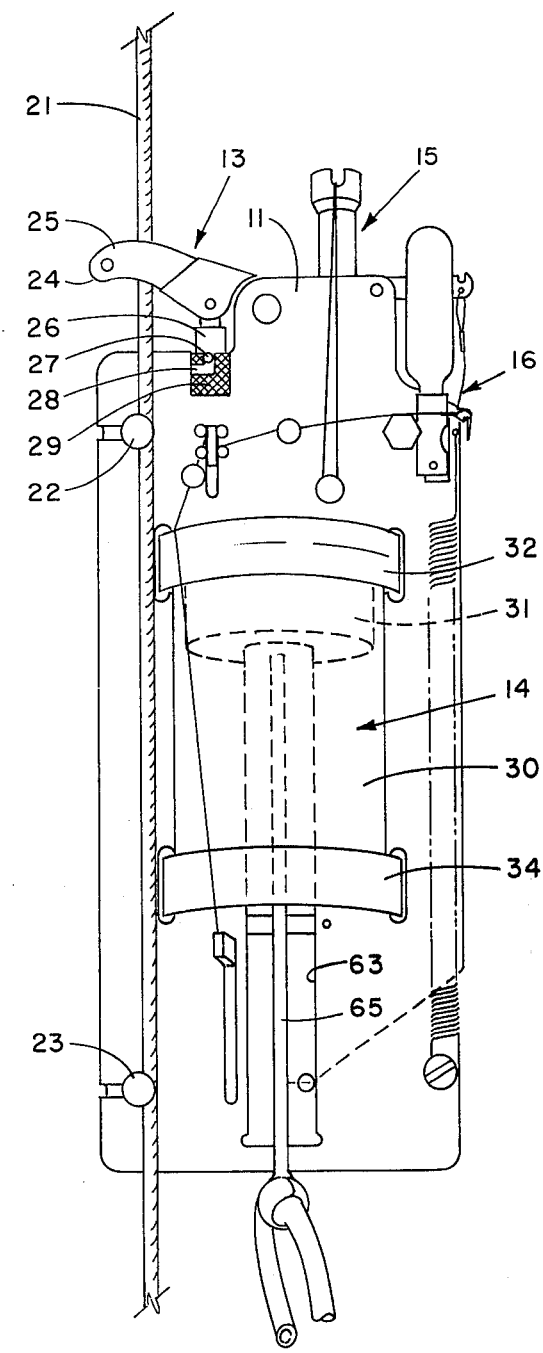
FIG. 1 is a perspective view of one embodiment of the invention.
Figure 2:
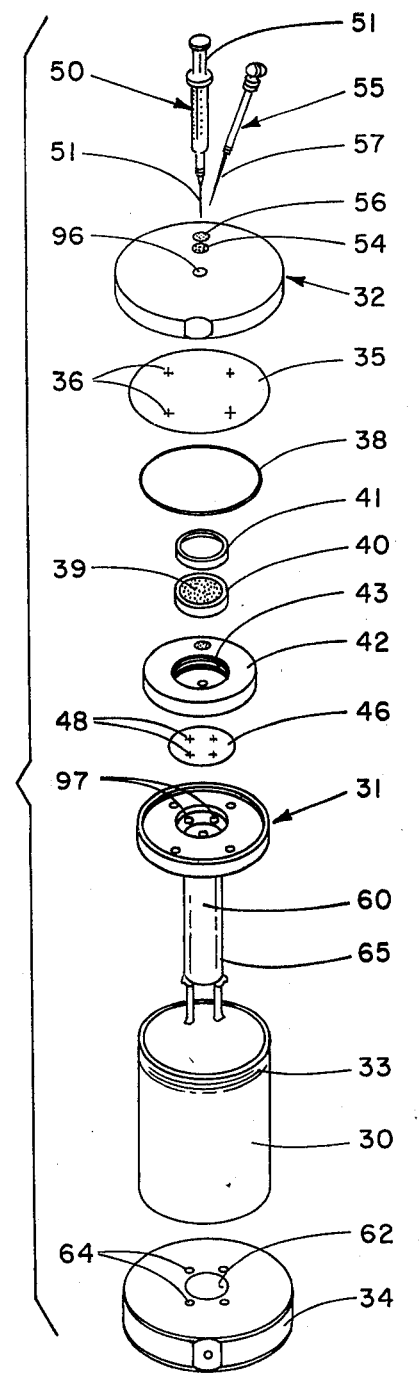
FIG. 2 is an exploded view in perspective of the essential components of the embodiment of FIG. 1.

Referring to the drawings, FIGS. 1 and 2 are perspective views of one embodiment of the invention which preferably includes a flat plate on which the components of the invention are mounted. These components include an actuating assembly 13, a sample receiving and retaining assembly 14, a labeling and tracing injector assembly 15 and an evacuating assembly 16. An exploded view of the components of sample receiving and retaining assembly 14 and some of the components of labeling and tracing injector assembly 15 is presented in FIG. 2. The major components of the foregoing assemblies are shown in FIG. 3.

The central structural member of the device is preferably a flat mounting plate 11 which is affixed to and suspended by a hydro wire 21 via a pair of hydro wire clamps 22 and 23 which are secured to plate 11. In assembly 13, hydro wire 21 passes through a yoke 24 in a trip lever 25 which is connected to a lever actuating rod 26 having a stud 27, stud 27 being aligned for movement in a slot 28 in a sleeve 29 which is rotatably mounted in plate 11 for permitting two-step actuation of the device by weighted messengers, not shown. A water sample is drawn or admitted into a chamber 30 by means of a piston 31, chamber 30 being screwed into an upper chamber cover 32 by means of threads 33 and supported by a perforated lower chamber cover 34. A one-way control valve and seal 35, which is circular in shape and preferably made of polyethylene, is positioned adjacent to upper chamber cover 32 and has cut into it a plurality of off-center slits 36 for admitting liquids into chamber 30. An O-ring 38, seated in a groove, not shown, in chamber cover 32 circumferentially seals valve 35 to the chamber cover. Samples are collected by a filter or filter pad 39 which is supported by a filter housing 40 and secured by a retaining ring 41 in a filter support platform 42 by means of internal threads 43 in platform 42. That is, retaining ring 41 secures filter pad 39 and filter housing 40 in place in filter support platform 42. A second one-way valve and seal 46 is positioned between filter 39 and piston 31 and also has cut into it a plurality of slits 48 for undirectionally passing liquids therethrough. A vertically disposed syringe 50 having a needle 51 therein is positioned above a sealed opening 54 in chamber cover 32, needle 51 when actuated passing through opening 54 which is filled preferably with silicone rubber. An angled cylinder 55 is positioned above another opening 56 in chamber cover 32 which opening is also filled with silicone rubber, cylinder 55 having a needle 57 disposed therein which when actuated passes through sealed opening 56 for admitting and controlling a flow of evacuating gas into chamber 30.

Figure 3:
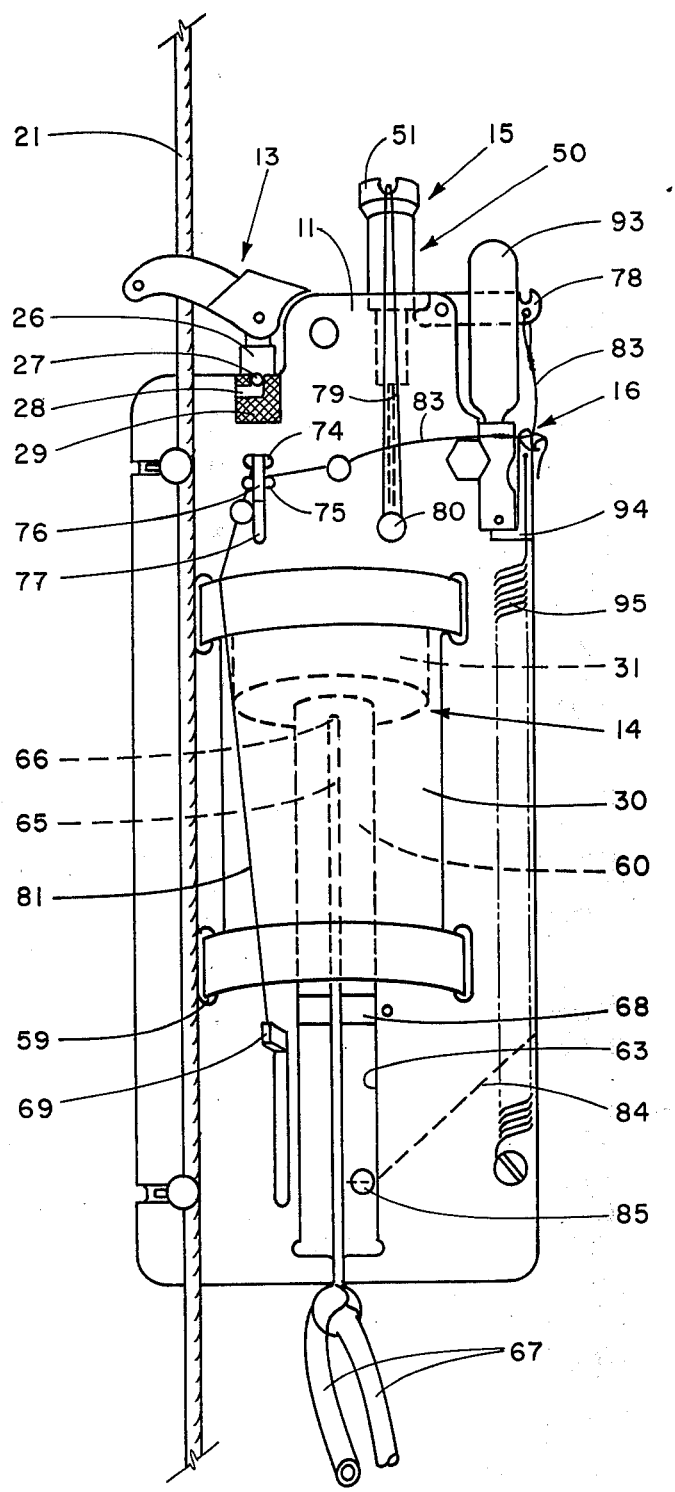
FIG. 3 is a schematic drawing of the embodiment of FIG. 1 illustrating operation of the invention.

Referring to FIG. 3, chamber 30 is centrally mounted in mounting plate 11 and protrudes equally from either side thereof between openings 58 and 59 therein, which accomodate the chamber covers, chamber 30 being secured to plate 11 preferably by set screws through the thin sides of the mounting plate in a conventional manner, not shown. Piston 31 is mounted on a piston rod 60 that extends through chamber 30, a bore 62 in support 34 and a void 63 in plate 11. Chamber 30 is free flooded below piston 31 through a plurality of orifices 64 in support 34. A latex spring 65 passes through longitudinal grooves, not shown, in piston rod 60 and a transverse groove 66 in the piston rod from a first position on the side of plate 11 seen which is indicated by knotted tags 67, upward through one groove in piston rod 60 and down the reverse side of the piston rod through the other groove to a similar knotted and tagged end, not seen. Spring 65 thus places piston 31 in tension with the piston prevented from being urged downward by a preferably metallic crossbeam 68 and a transverse arm 69. When latex spring 65 is released it urges piston 31 downward and as the piston descends chamber 30 is filled above the piston while unwanted water in chamber 30 below the piston is voided through orifices 64 in lower chamber cover and support 34.

Chamber 30 is filled with ambient water through the operation of a first messenger weight, not shown, which is dropped along hydro line 21 and which actuates trip lever 25 when it strikes this lever. Sleeve 29 is spring-loaded in a conventional manner by a torsion spring, not shown, so that when the first messenger weight strikes lever 25, stud 27 bottoms against the lower surface of transverse slot 28 thus stopping the downward movement of rod 26. At this time, the torsion spring interconnecting sleeve 29 in plate 11 rotates sleeve 29 counterclockwise, positioning stud 27 in another vertical slot, not shown, in sleeve 29 at the end of transverse slot 28 so as to permit further downward movement of pin 27 and rod 26 under the impact of a second messenger weight. Actuating assembly 13 further includes an upper release slot 74 and a lower release slot 75 for receiving ball detents which support an extension 76 of rod 26 in a slot 77 in selected positions after the impact of the messenger weights.

Syringe 50 preferably is positioned at the top of mounting plate 11 and needle 51 therein is held in spring-loaded engagement against a syringe latch 78 whose movement is restrained by a resilient means such as an elastic band 79 which is stretched between a holding means 80 on one side of plate 11 and a similar holding means, not shown, on the other side of plate 11. Transverse arm 69 is actuated by a cord 81 terminating in a ball received in upper release slot 74 while syringe latch 78 is actuated by a cord 83 terminating in a ball received in lower release slot 75. Cord 83 is further connected to a lanyard 84 whose end terminates in a ball 85 which is held in a slot, not shown, in plate 11 which disposes ball 85 in the path of piston rod 65 which rod dislodges ball 85 on its descent during the filling of chamber 30. When ball 85 is dislodged, lanyard 84 is released thereby releasing the restraining force on syringe latch 78 and permitting the tension of resilient means 79 to force needle 51 to eject the tracer fluid contained in syringe 50 into chamber 30 by piercing the rubber seal at opening 54 and piercing one-way polyethylene valve 35.

Cord 83 when released and latch 78 when actuated act to remove a safety means 90 which prevents accidental actuation of evacuating assembly 16. With pin 27 aligned for further longitudinal movement in response to a second messenger weight, the apparatus is set for the release of compressed gas contained in a tank 93 which release is accomplished when a lever arm 94 is actuated downward by a spring 95. In this condition, i.e. before action by the second messenger weight, the sample contained in chamber 30 may be incubated in the presence of the tracer treatment or other treatment, labeling means, etc. introduced via needle 51 for any desired period of time. At the conclusion of this time, a second messenger weight is released along hydro wire 21 which weight actuates trip lever 25, releasing restraining cord 83 and lever arm 94, thus allowing the tension in spring 95 to actuate arm 94. The end of arm 94, not shown, acts to pierce a seal in tank 93, releasing pressurized gas through a tube, not shown, into chamber 30 via cylinder 55 and actuated needle 57 which needle pierces a rubber seal in opening 56, polyethylene seal 35, filter pad 40 and polyethylene seal 46 and thereby enters chamber 30.

When a bottle has been deployed at the desired depth the first messenger weight is released, causing trip lever 25 to be partially depressed. This action releases spring-loaded arm 69 in turn releasing crossbeam 68 which then causes piston 31 to draw or admit a quantity of sample water into chamber 30 whose amount is determined by the volume of the chamber. That is, latex spring 65 is in tension when crossbeam 68 and arm 69 are in the condition shown in FIG. 3. Release of cord 81 by the action of the first messenger frees crossbeam 68 from restraint thereby allowing the tension in latex spring 65 to pull piston 31 downward which action ejects water below piston 31 through orifices 64 in support 34 and draws a water sample into chamber 30 through a fill hole 96 in chamber cover 32 and slits 36 in valve 35. The filter assembly comprising filter pad 39, filter housing 40, ring 41 and platform 42 is withdrawn with piston 31, the action of one-way valve 46 preventing the escape of water through the filter assembly on filling of chamber 30. Sample matter is collected by filter 40 when the chamber is evacuated.

During its downward travel the butt end of piston rod 63 unseats ball 85 attached to lanyard 84 near the end of the piston travel when chamber 30 is substantially full, releasing lanyard 84 and also releasing latch 78. Upon being released, latch 78 allows needle 51 under the urging of elastic band 79 to penetrate into chamber 30 through sealed opening 54 and valve 35, the piston and labeling assembly 14 having been moved to the bottom of chamber 30 and the chamber having been filled. This action forces the contents of syringe 50 into chamber 30 so that chamber 30 now contains the desired water sample as well as the desired treating or labeling liquid and these contents of chamber 30 may be maintained undisturbed in the chamber until it is evacuated.

After a selected period of incubation of any particulate matter in the water sample in chamber 30, the second messenger is released along hydro wire 24 which upon arrival further actuates trip lever 25 and pin extension 76 so as to release cord 83. This release of cord 83 removes the remaining restraints on lever 94, allowing the tension in spring 95 to actuate lever 94 and release pressurized gas into chamber 30 via needle 57 in cylinder 55 which needle is injected through sealed opening 56 in valve 35. As stated above, piston 31 now is at the lower end of chamber 30 so that the angled entry of needle 57 is not impeded. One-way valve 46 opens during venting, allowing the water sample in the chamber to pass through filter pad 39 where particulate matter is collected, through slits 48 in valve 46 and through a plurality of orifices 97 in piston 31 and orifices 70 in lower chamber cover 34 which all preferably are in register.

In summary, the sampler's functions include the first messenger weight striking trip lever 25 and partially depressing the lever thereby releasing cord 81 and transverse arm 69 which in turn releases crossbeam 68 so as to permit downward movement of piston 31 and piston rod 60 under the urging of spring 65. This action permits the piston and piston rod to descend until piston rod 60 traverses void 63, releasing ball 85 and lanyard 84 near the end of its travel. The first actuation of trip lever 25 thus generates a sequence of events which includes freeing upper slot 74 of lanyard 81, permitting arm 69 to drop thereby releasing piston rod 60, urging piston rod 60 to descend under the tension of spring 65, dislodging ball 84 and releasing lanyard 85, releasing latch 78 which then permits resilient means 79 to urge syringe needle 51 in syringe 50 to be depressed thereby directly injecting liquid or other matter into chamber 30. Syringe needle 51 passes through rubber-filled hole 54 in chamber cover 32 and through one-way valve 35, entering chamber 30 directly thereafter. The second actuation of trip lever 25 by the second messenger weight further depresses trip lever 25 causing the release of cord 83 which was secured in lower release slot 75, this action freeing restraining means 90 and thereby firing arm 94 which causes bottle 93 to be punctured via the urgency of spring 95. Gas from cylinder 93 is directed into chamber 30 through needle 57 or cylinder 55, this needle entering the chamber through rubber-sealed opening 54 in chamber cover 32 and valve 35. The gas entering chamber 30 generates positive internal pressure therein which acts from below to close valve 35 and from above to open valve 46, forcing the water sample in chamber 30 out through filter pad 40, holes 97 in piston 31 and holes 70 in lower chamber cover 34. Particulate matter in the sample is intercepted by filter pad 40 as the sample passes therethrough.

There is thus provided a sampler which allows carbon 14 tracer or other treated organic or other material in a given volume of water to be collected under in situ conditions, i.e. pressure, temperature and light intensity. The sampler is adaptable for basic research in a variety of oceanographic or other studies. The material in the sample is maintained under ambient conditions until analyzed, thereby avoiding inaccuracies due to changing environmental conditions as well as contamination occasioned by conventional systems which subject the sample to changing environmental conditions and additionally to contamination during a laboratory-conducted separation procedure. The in situ separator of the present invention will perform at any time during operation of the device without removal from the sampling depth. The system not only provides for the injection of tracer or other liquid in situ but separates the free water phase from the labeled material in the sample after any desired time of incubation. The material collected in situ by the filter is immediately available for laboratory analysis upon removal of the filter from the already evacuated sample chamber.

The present in situ separator is reliable in operation and corrosion therein is minimized because of the metals used, e.g. 316 stainless steel and other compatible metals, in the actuating mechanisms and the use of synthetic materials such as plexiglass and polyvinylchloride in other components. Since the separator operates completely in situ and no lubricants are used or required on the equipment, freedom from contamination is substantially assured for the sample. The separator should also be very useful on projects where the validity of the results is adversely affected by inability to control variables such as temperature, pressure and light intensity to within the in situ range of magnitude.

Obviously many modifications and variations of the present invention are possible in the light of the above teachings. For example, the evacuating gas could be regulated so as to be selectively released regardless of the ambient hydrostatic pressure, and the dual messenger-actuated controls could be adapted to perform other 2-phase in situ operations than those disclosed.

What is claimed is:

1. A deep water sampling device and in situ separator of particulate matter comprising:
    a cylindrical sample chamber having end closure means;
    means for admitting ambient water into said chamber at a selected depth;
    a labeling liquid in said device and means for introducing said liquid in situ into said chamber upon said chamber receiving a selected volume of ambient water;
    means for retaining particulate matter in said device upon evacuation of said volume of water; and
    means for evacuating in situ said volume of water, whereby particulate matter may be separated from a water sample in situ and examination and counting thereof may be commenced as soon as said device is retrieved and said retaining means is removed from the device.

2. The device defined in claim 1 wherein said means for introducing liquid in situ and said means for evacuating in situ are independently actuated so that the labeled particulate matter may incubate for any selected period of time under normal ambient conditions.

3. The device defined in claim 2 wherein said means for admitting water into said chamber is a messenger-actuated trip lever; and
    a hydrographic wire for suspending said device at selected depths and first and second weighted messenger means adapted for passing down said hydrographic wire and independently actuating said trip lever,
    said trip lever when actuated by said first messenger means actuating said means for introducing liquid into said chamber and arming of said evacuating means,
    said trip lever when actuated by said second messenger means actuating said means for evacuating in situ and accomplishing the removal of particulate matter from the water sample being evacuated by said means for retaining particulate matter.

4. The device defined in claim 3 and further including a piston rod and a piston mounted on one end thereof in said chamber;
    said piston in the top position in said chamber on lowering of said device,
    said piston rod extending through said chamber in sealed relationship therewith;
    piston actuating means positioned outside of said chamber in the path of said piston rod; and
    guide means in said device for defining the path of said piston rod,
    said actuating means actuating said means for introducing liquid after a selected movement of said piston rod.

5. The device defined in claim 4 wherein said chamber is free-flooded during descent through one of said end closure means and a sample is admitted at the desired depth into the chamber through a fill report in the other of said end closure means upon operation of said means for introducing liquid into said chamber,
    said other of said end closure means including a first one-way valve operable only to admit water into said chamber; and a second one-way valve in said means for retaining particulate matter operable only to void water from said chamber through said one of said end closure means after filling of said chamber in situ.

6. A method of obtaining and separating particulate matter from ambient water in situ at any depth comprising:
admitting water into an exposed sample collecting chamber in a sampler upon immersion of the sampler;
voiding the water in the chamber at a selected depth and admitting ambient water thereinto at said depth;
injecting particle treating material into the ambient water sample;
incubating the treated ambient water sample for any desired period of time; and
voiding the treated ambient water sample through a filter means at said selected depth,
whereby treated particulate matter which has been selectively incubated in situ is immediately available for laboratory analysis upon retrieval of the sampler and removal of the filter means.

7. The method of claim 6 wherein said water initially in said chamber is voided simultaneously with the admission of ambient water thereinto.

8. The method of claim 7 wherein said water initially in said chamber and said ambient water sample are voided through a common voiding means in said sampler.

9. The method of claim 8 wherein said chamber is sealed after collection therein of said ambient water sample and said particle treating material is introduced into said sample by means penetrating the means sealing said chamber.

10. The method of claim 9 wherein said ambient water sample is evacuated after incubation by pressurized gas admitted into said chamber through additional means penetrating the means sealing said chamber.

11. The method of claim 10 wherein the introduction of said particle treating material and said pressurized gas is accomplished by actuating individual system means in said sampler via passing separate messenger weights along the wire suspending said sampler at a time interval determined by the desired length of said incubation period.

12. A sampling device for in situ incubation and separation of particulate matter of an ambient sample at any depth comprising:
a sample container operable at the selected depth;
means connected to said container for collecting a sample of ambient water therein at any desired time;
means in said device for introducing in situ particulate matter treating material into the ambient water sample; and
means in said device and said container for voiding in situ the ambient water sample while retaining the particulate matter therein of a selected size and larger,
whereby particulate matter may be collected, incubated and separated in situ so as to be made available for immediate examination and counting upon removal from said device.

13. The device defined in claim 12 wherein said means for collecting a sample includes a container upper end closure having a fill port for liquids and sealed entry means;
a container lower end closure having a piston bore and voiding ports for liquids;
a piston and a piston rod in said container and means connected thereto and to said device for moving said piston from one end of said container to the other end thereof;
a particle filtering assembly adapted to be received in said piston; and
undirectional valve means disposed between said upper end closure and said filtering assembly and between said filtering assembly and said piston to restrict movement of water through said container to one direction,
said container free-flooded through said voiding ports upon lowering of said device,
said piston normally disposed adjacent said upper end closure and when urged downward voiding the water in said container below said piston and drawing a water sample thereinto above said piston through said fill port,
said undirectional valve means permitting entry and retention of said water sample in said container.

14. The device defined in claim 13 wherein said means for moving said piston is a first resilient member normally in tension,
releasable means connected to said device for preventing movement of said piston and piston rod by said first resilient member;
a hydrographic wire suspending said device and means deployed adjacent said hydrographic wire for releasing said releasable means at a selected time; and
a first messenger weight adapted to pass along said hydrographic wire and actuate said means deployed adjacent said hydrographic wire.

15. The device defined in claim 14 wherein said means for introducing treating material into said ambient water sample is a syringe mounted on said device;
a needle in said syringe and releasable means restraining said needle from movement;
a second resilient member connected between said needle and said device for maintaining said needle in tension; and
means disposed in the path of said piston rod and actuable thereby when said container is substantially filled with said ambient water sample for releasing said means restraining said needle so that when so released said needle will enter said container through one of said sealed entry means and inject treating material thereinto.

16. The device defined in claim 15 wherein said means deployed adjacent said hydrographic wire further includes means arming said means restraining said needle for actuation by said first messenger weight so that premature movement of said needle is precluded.

17. The device defined in claim 16 wherein said means for voiding includes a capsule mounted on said device and a pressurized gas in said capsule, means for directing said gas into said container through another of said sealed entry means, means for releasing said gas upon additional actuation of said means for releasing said releasable means by a second messenger weight, a second messenger weight adapted to be passed along said hydrographic wire, and means preventing operation of said means for releasing said gas until release of said releasable means preventing movement of said piston rod.

* * * * *